000
United States Patent [19]
Shigeta et al.

[11] Patent Number: 4,803,158
[45] Date of Patent: Feb. 7, 1989

[54] COMPOSITION USED FOR THE DETERMINATION OF BETA-HYDROXYBUTYRIC ACID AND A METHOD FOR PREPARING THE SAID COMPOSITION

[75] Inventors: Yukio Shigeta, Hyogo; Yutaka Harano, Shiga; Shigeki Yamada, Kyoto; Yoshinori Takahaski, Fukui, all of Japan

[73] Assignees: Kabushiki Kaisha Kyoto Daiichi Kagaku; Kabushiki Kaisha Sanwa Kagaku Kenkyusho, both of Japan

[21] Appl. No.: 922,178

[22] Filed: Oct. 23, 1986

Related U.S. Application Data

[63] Continuation-in-part of Ser. No. 582,059, Feb. 21, 1984, abandoned.

[30] Foreign Application Priority Data

Mar. 8, 1983 [JP] Japan .................................. 58-39813

[51] Int. Cl.$^4$ ........................... C12Q 1/32; C12Q 1/26
[52] U.S. Cl. ........................................ 435/25; 422/57; 427/2; 435/26; 435/805
[58] Field of Search ..................... 422/57; 435/26, 805, 435/25; 427/2

[56] References Cited

U.S. PATENT DOCUMENTS

| | | | |
|---|---|---|---|
| 3,630,957 | 12/1971 | Rey et al. ............................ | 435/805 |
| 4,254,222 | 3/1981 | Owen .................................... | 435/26 |
| 4,273,870 | 6/1981 | Möllering et al. ..................... | 435/26 |
| 4,351,899 | 9/1982 | Owen .................................... | 435/26 |
| 4,356,149 | 10/1982 | Kitajima et al. ..................... | 435/805 |
| 4,567,024 | 1/1986 | Koyama et al. ..................... | 435/805 |

*Primary Examiner*—Robert J. Warden
*Assistant Examiner*—David A. Saunders
*Attorney, Agent, or Firm*—Darby & Darby

[57] ABSTRACT

This invention relates to a composition for determining β-hydroxybutyric acid, usable for doctors, nurses, and patients themselves simply and quickly without use of special instruments, and also relates to a method for preparing the said composition.

The composition of the invention oxidizes β-hydroxybutyric acid under alkaline conditions and the presence of nicotineamide adenine dinucleotide (NAD) by β-hydroxybutyric acid dehydrogenase, and the produced reduction-type NAD (NADH) reduces tetrazolium salt through an electron carrier to produce formazan developing color. The composition permits accurate measurement quickly and simply, and has excellent conservative stability, because it is a uniform solid-phase composition prepared by applying reagents necessary for the reaction of film impermeable to water together with a natural or synthesized film forming polymer. The invention further provides a method for preparing the said composition by applying, on a supporter impermeable to water, W/O emulsion which is formed by dispersing alkaline buffer, β-hydroxybutyric acid dehydrogenase, NAD, electron carrier, and tetrazolium salt in an organic solvent insoluble in water together with a natural or synthesized film forming polymer.

3 Claims, 2 Drawing Sheets

COMPOSITION USED FOR THE DETERMINATION OF BETA-HYDROXYBUTYRIC ACID AND A METHOD FOR PREPARING THE SAID COMPOSITION

This is a continuation-in-part of copending application Ser. No. 582,059, filed on Feb. 21, 1984, now abandoned. The entire disclosure of the parent application is incorporated by reference.

BACKGROUND OF THE INVENTION

This invention relates to a novel uniform solid-phase composition which makes possible simple and rapid determination of $\beta$-hydroxybutyric acid and to a method for preparing the said composition.

$\beta$-Hydroxybutyric acid, a kind of ketone body, is an intermediate product of fatty acid metabolism and is found in large quantities in the body fluids (blood, urine, etc.) of diabetes patients and diabetes animals. The invention is hereinafter described in detail on the case of determining $\beta$-hydroxybutyric acid in body fluids.

A carbohydrate metabolic disorder such as insulin deficiency due to pancreas incretion disorder causes fatty acid oxidation in the liver to increase. This results in abnormally increased ketone bodies such as acetone, acetoacetic acid, and $\beta$-hydroxybutyric acid, which are excessively accumulated in tissues, blood, and urine (ketosis state). It is necessary, therefore, in the case of high-degree pancreas incretion disorder, particularly serious diabetes, or when dosing a patient with carbohydrate limiting food, to pay attention to the ups and downs of the ketone bodies in the body fluid.

It is generally said that when ketosis state occurs in series diabetes, $\beta$-hydroxybutyric acid of these ketone bodies in the blood remarkably increases, resulting in increased ($\beta$-hydroxybutyric acid)/(acetone+acetoacetic acid) ratio, and thus most sharply indicates abnormal metabolism.

A known quantitative determination method of $\beta$-hydroxybutyric acid is the method by Williamson et al which uses a $\beta$-hydroxybutyric acid dehydrogenase (Biochemical Journal, Vol. 82, p. 90, 1962). In this method, $\beta$-hydroxybutyric acid is reacted with $\beta$-hydroxybutyric acid dehydrogenase and diphosphopyridine nucleotide (DPN), and the absorbance of the produced diphosphopyridine nucleotide of reduced type (DPNH) is measured at the specific absorption of 340 nm. The quantity of $\beta$-hydroxybutyric acid is determined from the molecular extinction coefficient. Accordingly, there are problems that a high-class ultraviolet spectrophotometer is required, and high skill and long period of time are needed in analysis.

To eliminate such drawbacks, there has been developed a simple colorimetry of high-sensitivity of ketone body in blood, which requires no ultraviolet spectrophotometer (Tokkai Sho 55-035232). In this method, $\beta$-hydroxybutyric acid is first acted with $\beta$-hydroxybutyric acid dehydrogenase and nicotineamideadenine dinucleotide (NAD) to be oxidized enzymatically into acetoacetic acid, and then reacted with p-nitrophenyldiazonium fluoroborate into an azo compound, together with the acetoacetic acid contained originally in the blood. The azo compound is reduced with hypophosphorous acid into a stable hydroazo compound, and the total acetoacetic acid is determined by colorimetry of the hydroazo compound by use of the wave length of 390 nm. Separately, only the acetoacetic acid originally contained in the blood is measured by similar colorimetry but without action of $\beta$-hydroxybutyric acid dehydrogenase. The above total quantity of acetoacetic acid is subtracted by this acetoacetic acid quantity to give the quantity of $\beta$-hydroxybutyric acid in the blood. This method, however, has still had a number of problems as a daily clinical examination method, requiring high skill and long time for measurement because of pretreatment (protein removal) of the blood sample and complex operation, and needing special utensils and a high-class spectrophotometer.

As the simpler examination measure, there is Owen's tester for determining $\beta$-hydroxybutyric acid (U.S. Pat. No. 4,351,899). Owen's tester has two absorptive test surfaces wherein the first absorptive test surface contains tetrazolium salt, NAD, and electron transporter, and dried residue of $\beta$-hydroxybutyric acid dehydrogenase, and the second absorptive test surface contains dried residue of pH buffer. In using the test indicator, the first test surface is put on the second test surface, and a material is dropped on them, and the concentration of $\beta$-hydroxybutyric acid in the material can be measured by reading the hue after 2 min from dropping. It maintains the stability of the test indicator that it has two absorptive test surfaces. Owen states that if tetrazolium salt, NAD, an electron carrier, $\beta$-hydroxybutyric acid dehydrogenase, and pH buffer for maintaining pH in alkaline side, which are reagents necessary for determining $\beta$-hydroxybutyric acid, are dissolved in one solution, color development occurs.

Owen's test indicator has surely made a progress in simplicity. However, it is troublesome that a sample has to be dropped on the two absorptive test surfaces put on each other after taken out from separate vessels for drying. Further, although both reagents on the first and second absorptive test surface have to be dissolved uniformly to advance the reaction quantitatively, only dropping a sample on the two absorptive surfaces put on each other can not provide a uniform reaction condition. Accordingly, Owen's test indicator is lacking in quantitativity as a major problem.

SUMMARY OF THE INVENTION

It is an object of the invention to provide a stable composition for $\beta$-hydroxybutyric acid determination which eliminates the drawbacks of the conventional techniques and can be used by physicians, nurses, as well as patients themselves quickly and simply without using special instruments.

Another object of the invention is to provide a method for preparing the said composition.

As the result of assiduous study to attain these objects, the inventors have found a stable composition for determining $\beta$-hydroxybutyric acid made in one united body by using high molecular polymer, in which $\beta$-hydroxybutyric acid is dehydrogenated by $\beta$-hydroxybutyric acid dehydrogenase at pH 7–9 under the presence of nicotineamideadenine dinucleotide (NAD), and the produced NAD of reduced type (NADH) reduces tetrazolium salt through electron transporter, and the color degree of the produced formazan is measured to determine $\beta$-hydroxybutyric acid.

Further, the inventors have found that the stablest composition of little background color can be obtained by using 1-methoxy PMS or diaphorase as electron transporter and using nitro-TB (3,3'-dimethoxy-4,4'-biphenylilene-bis[2-(p-nitrophenyl)-5-phenyl-2H.tetrazolium]) as tetrazolium salt.

In preparing the composition of the invention, β-hydroxybutyric acid dehydrogenase, NAD, electron transporter, and pH buffer for maintaining pH at 7-9 during the reaction are dissolved together with a high molecular polymer, then tetrazolium salt is dissolved, and then the solution is applied on a surface impermeable to liquid and dried.

Particularly, a stable test composition of no color development on the composition itself can be prepared by the following method. A solution, in which β-hydroxybutyric acid dehydrogenase, NAD, tetrazolium salt, and buffer are dissolved together with a hydrophilic high molecular polymer, is mixed with a solution dissolved a film forming polymer in organic solvent insoluble in water, and W/O emulsion formed by dispersing is uniformly applied on a supporter impermeable to water.

Figure 1:
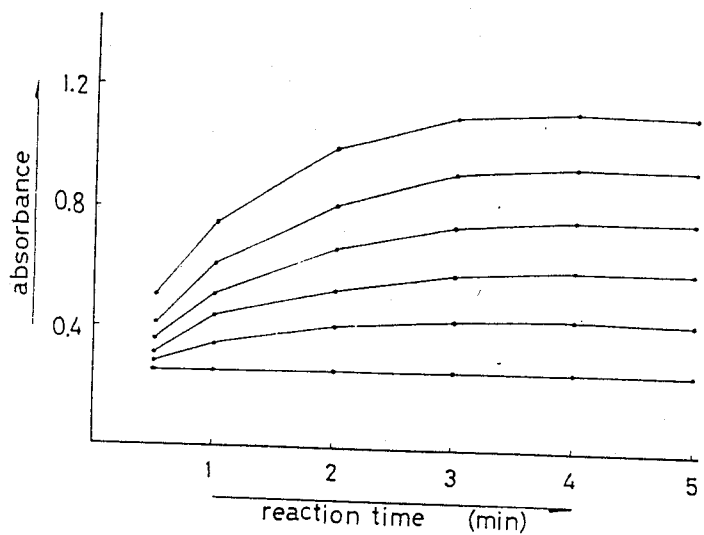
FIG. 1 is a diagram showing the reaction time course by the recipe of Reference Example 1 according to the invention.
Figure 2:
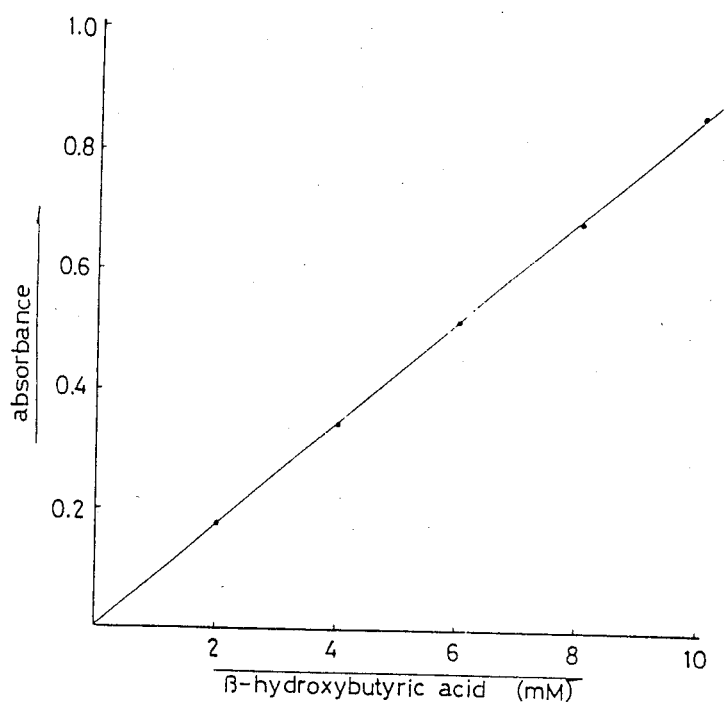
FIG. 2 shows a calibration curve for the recipe of Reference Example 1 according to the invention.

(1) FIG. 1 (2) Absorbance (3) Reaction time(min) (4) FIG. 2 (5) β-Hydroxybutyric acid(mM)

DETAILED DESCRIPTION OF THE INVENTION

According to the measurement principle of the invention, β-hydroxybutyric acid is first dehydrogenated by β-hydroxybutyric acid dehydrogenase at pH 7-9 under the presence of an electron acceptor, NAD, into acetoacetic acid, as shown below. The reduced type NAD (NADH) produced here reduces tetrazolium salt through an electron transporter into colored formazan. The color comparison of this formazan gives the quantity of β-hydroxybutyric acid.

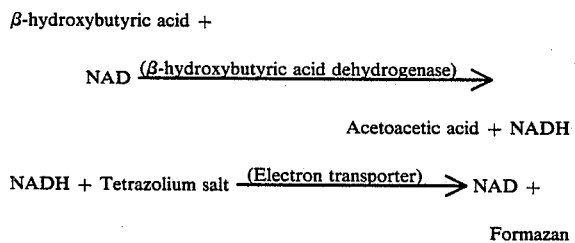

β-hydroxybutyric acid +

NAD $\xrightarrow{\text{(β-hydroxybutyric acid dehydrogenase)}}$

Acetoacetic acid + NADH

NADH + Tetrazolium salt $\xrightarrow{\text{(Electron transporter)}}$ NAD + Formazan Making use of the principle, when a drop of the specimen is applied on the composition of the invention prepared dexterously, color corresponding to the concentration of β-hydroxybutyric acid in the specimen appears on the composition after several minutes. Only comparing this by the naked eye with the standard color table prepared in advance provides determination of the β-hydroxybutyric acid concentration. The composition may be added with various additives, as required, such as retaining agents, stabilizers, and reaction accelerators.

Owen (U.S. Pat. No. 4,351,899) states that in case β-hydroxybutyric acid dehydrogenase, NAD, electron transporter, tetrazolium salt, and pH buffer for providing a pH condition appropriate to the reaction, which are used for the measurement principle of the invention, are united into one solution, the solution developes color. The inventors examined this problem.

According to the recipe of Example 1 by Owen (U.S. Pat. No. 4,351,899), the impregnating solution for the first absorptive test surface and that for the second one were separately prepared, and when a mixed impregnating solution was prepared by uniting both solutions, immediately the solution was colored purple. When absorptive paper (corresponding to Eaton Dikeman Paper #204, Filter Paper #50 made in Toyoroshi) was dipped in this mixed impregnating solution and air dried, the prepared test indicator itself was colored dark purple, being entirely unusable as test paper. As Owen stated, the presence of buffer for pH 8.8 resulted in a unusable state because of the color development on the test surface.

The recipe of Example 1 by Owen (U.S. Pat. No. 4,351,899)

Impregnating solution for the first absorptive test surface

| | |
|---|---|
| (1) β-Hydroxybutyric acid dehydrgenase | 60 IU/ml |
| (2) NAD | 21 mM |
| (3) Meldola blue | 0.25 mM |
| (4) INT | 8.9 mM |
| (5) Tetrazolium reducing catalyst (K$_2$PdCl$_4$) | 0.1 mM |
| (6) Formazan stabilizer Triton X-100 | 1% V/V |

Impregnating solution for the second absorptive test surface

| | |
|---|---|
| Glycine-sodium hydroxide Buffer | 1 M (pH 8.8) |
| Monopotassium phospate-dipotassium phosphate Buffer | 1 M (pH 8.8) |
| Equivolume mixture of the above both buffers | |

The first and second absorptive test surfaces were prepared truly according to Example 1 in Owen's Patent, and both were put separately into airtight vessels shading the light in the presence of a sufficient amount of a drying agent (silicagel). In storing at 40° C., the color of the first absorptive test surface added purple to the original pale blue after 10 hr, and indicated deep purple after 20 hr, indicating the similar hue with one developed from the liquid sample containing relatively high concentration (2 mM) of β-hydroxybutyric acid. In storing at 25° C., the above mentioned hue was indicated after about 2 weeks. A tester with such degree of conservative stability is lacking in practicality as one for determining β-hydroxybutyric acid in body fluids, being unable to be offered to users as goods.

When serum containing 0.5 mmol/l of β-hydroxybutyric acid was applied on this tester and the color reaction was observed, it took 2 min until apparent color development and 6 min untill above a definite deepness of color, substantially requiring a longer reaction time than the tester of the invention. This is because the tester is composed of two test surfaces and the carrier of ingredients is paper.

In view of the above conditions, as the result of assiduous study to find a composition of excellent conservative stability for determining β-hydroxybutyric acid, the inventors have found that using NTB as diazonium salt and 1-methoxy PMS as electron transporter reduces the color of the solution itself even when all reagents necessary for the reaction are dissolved in a liquid.

Further, the inventors have found that using natural or synthesized film forming polymer as binder of ingredients of the composition in these reagents solutions improves the conservative stability, and found that a composition of excellent conservative stability and of no color on the composition itself can be prepared by dissolving lastly tetrazolium salt in preparing impregnating solution containing natural or synthesized binder and by applying immediately and drying. Only a hydrophilic binder may be used, or a hydrophilic binder dispersed in a hydrophobic binder may be used.

The β-hydroxybutyric acid dehydrogenase used in the invention may be any one which can oxidize β-hydroxybutyric acid into acetoacetic acid, including those derived from bacteria such as *Rhodopseudomonas spheroides* and *Pseudomonas lemoigneis* and those extracted from animal tissues such as the heart of cattle and liver of pig.

The NAD used in the process of the invention is a coenzyme which exhibits hydrogen atom acceptance action in oxidation-reduction system reaction, including those extracted from animal tissues such as the liver and kidney and from yeasts. Their sodium salts and lithium salts are also usable.

The electron transporter used in the invention may be any one which can activate the hydrogen donating action of produced NADH, typified by diaphorase, a kind of flavin enzyme, and intermediate electron transporters such as 9-dimethylaminobenzo-α-phenazoxonium chloride (shortened as Meldoa blue), N-methylphenazonium methosulfate (shortened as PMS), and 1-methoxy-5-methylphenazonium methylsulfate (shortened as 1-methoxy PMS). The particularly preferable are 1-methoxy PMS and diaphorase which are stable.

The tetrazolium salts are reduced to formazans, colored substance, under the presence of reducing substances and include many monotetrazolium salts and ditetrazolium salts. The typical examples of the former are 3-(p-iodophenyl)-2-(p-nitrophenyl)-5-phenyltetrazolium chloride (shortened as INT) and 3-(4,5-dimethyl-2-thiazolyl)-2,5-diphenyl-2H-tetrazolium bromide (shortened as MTT). The typical examples of the latter are 3,3'-(3,3'-dimethoxy-4,4'-biphenylylene)-bis-(2,5-diphenyl-2H-tetrazolium chloride) (shortened as TB) and 3,3'-(3,3'-dimethoxy-4,4'-biphenylylene)-bis-[2-(paranitrophenyl)-5-phenyl-2H-tetrazolium] (shortened as nitro-TB). Of these compounds, preferable is nitro-TB which is readily soluble in water and relatively stable.

Hydrophilic natural or synthesized organic film forming polymers are gum arabic, alginic acid, gelatin, dextran, prulan, carboxymethylcellulose, hydroxypropylcellulose, polyvinyl alcohol, and sodium polyacrylate. Hydrophobic binders are ethylcellulose, celluloseacetate, ethylpolyacrylate, polyvinylbutyral, polyvinylacetate, and polyvinylcarbazole. Of these compounds, preferable hydrophilic binders are gelatin and polyvinyl alcohol, and preferable hydrophobic binders are ethylcellulose and polyvinylbutyral.

The pH buffer used in the invention may be any one which gives best pH conditions (7-9) to enzyme reaction and color reaction and includes phosphoric acid buffer, boric acid buffer, tris buffer, and Good's buffer which are able to maintain above pH conditions. Other additives can also be used.

The above reagents are dissolved, for example, in water, and the aqueous solution is applied with an addition of a binder on a supporter such as polyester film to a thickness. The supporter, after being dried, is cut, for example, to about 5 mm square to form a test piece and adhered to an end of a strip of plastic film.

When a sample of body fluid such as serum, blood plasma, and urine is dropped on the test piece, it develops color after several minutes. When the sample is a whole blood, forming a semipermeable layer which allows low-molecular substances such as β-hydroxybutyric acid to pass through it but does not allow macro substances such as red corpuscle, permits observation of the color on the test piece without interference by red color of the corpuscles, since the corpuscles can be washed or wiped off after color reaction. The developed color is compared by the naked eye with the standard color table which has been prepared in advance and gives the concentration of β-hydroxybutyric acid in the body fluid. It is possible to obtain a higher accuracy of the measurement by using a simple reflectmeter having a light source corresponding to the developed hue.

Examples found in the process of the study are described to help to understand the invention as Reference Examples in the following.

REFERENCE EXAMPLE 1

A reagent was prepared by dissolving 10 mg of β-hydroxybutyric acid dehydrogenase (origin: *Pseudomonas lemoigneis*, relative activity: 10 U/mg), 33 mg of NAD, 3 mg of an electron transporter (1-methoxy PMS), and 17 mg of tetrazolium salt (nitro-TB) in 100 ml of 0.1M-trishydroxyaminomethane-hydrochloric acid buffer solution (pH 8.5).

Each 3.0 ml of this reagent was put in test tubes, and each 20 μl of aqueous β-hydroxybutyric acid solution (standard solutions: 0, 2, 4, 6, 8, 10 mmol/l) was added to the respective test tubes. The absorbance of each mixture was measured after being held at 37° C. for 0.5, 1, 2, 3, 4, and 5 min by a colorimeter with monochromatic light of 520 nm. The results are shown in Table 1.

TABLE 1

| Reaction time | 0.5 min | 1 min | 2 min | 3 min | 4 min | 5 min |
|---|---|---|---|---|---|---|
| 0 mM | 0.257 | 0.260 | 0.263 | 0.264 | 0.263 | 0.264 |
| 2 mM | 0.282 | 0.346 | 0.407 | 0.434 | 0.440 | 0.441 |
| 4 mM | 0.308 | 0.437 | 0.533 | 0.591 | 0.609 | 0.608 |
| 6 mM | 0.363 | 0.512 | 0.669 | 0.752 | 0.784 | 0.782 |
| 8 mM | 0.406 | 0.607 | 0.810 | 0.915 | 0.949 | 0.952 |
| 10 mM | 0.511 | 0.748 | 1.008 | 1.106 | 1.129 | 1.131 |

To show the reaction time course, FIG. 1 was plotted with the reaction time as the abscissa and the absorbance as the ordinate. From FIG. 1, it was found that the reagent itself is little colored in view of the change of absorbance in the sample of 0 mmol/l and the reaction reaches the end point in about 4 min.

Further, a calibration curve (FIG. 2) was drawn up with the absorbance of each standard solution measured after 4 min where the reaction had reached the end point (subtracted by the absorbance 0.263 of 0 mol/l, a blank value) as the ordinate and the concentration of the standard solutions as the abscissa. A straight line up to 10 mol/l of β-hydroxybutyric acid through the origin was obtained.

Twenty microliters of a patient serum specimen was added to 3.0 ml of reagent of the above recipe, and the mixture was reached at 37° C. for 5 min. The absorbance of the mixture measured using a monochromatic light of 520 nm was 0.27. From the calibration curve of FIG. 2, the concentration of β-hydroxybutyric acid in the specimen is 3.10 mmol/l.

As revealed in this Example, β-hydroxybutyric acid can be determined even in a single reagents solution at pH 8.8 by using 1-methoxy PMS as electron transporter and nitro-TB as diazonium salt.

Thus, this method enables the determination of β-hydroxybutyric acid in the specimen by adding 20 μl of the specimen to 3.0 ml of the reagent of the above recipe, reacting the mixture at a certain temperature for 4–5 min, measuring the absorbance of a monochromatic light around 520 nm by the reacted mixture, and by reference of the absorbance to the calibration curve prepared in advance under the same conditions.

REFERENCE EXAMPLE 2

To reveal the difference between the tester described in Example 1 by Owen and the composition of the invention, a test piece wherein all reagents necessary for determining β-hydroxybutyric acid were impregnated in one absorptive carrier was prepared by using 1-methoxy PMS as electron transporter and nitro-TB as tetrazolium salt and by adding cattle serum albumin.

One milligram of 1-methoxy PMS, 100 mg of cattle serum albumin as stabilizer, and 50 U of β-hydroxybutyric acid dehydrogenase (origin: *Pseudomonas lemoigneis*) were dissolved in 10 ml of 0.1M boric acid-borax buffer solution (pH 8), and then nitro-TB was dissolved, and immediately filter paper was dipped in this solution and air-dried at room temperature. In this time, the filter paper so slightly colored blue as not to give an influence on the determination of β-hydroxybutyric acid.

The dried filter paper was cut into a 5-mm square test piece and adhered to the end of a 5×70 mm strip of PVC film with double coated adhesive tape. The test piece was dipped in the specimen or a drop of the specimen was applied on the test piece. After 3 min of reaction, blue-purple color was developed on the test piece. The concentration of β-hydroxybutyric acid in the specimen could be determined by comparing the hue of the developed color with the standard color table, prepared in advance, showing the hue of developed color corresponding to 0, 0.1, 0.2, 0.5, 1.0, 2.0, 5,0, and 10.0 mmol/l of β-hydroxybutyric acid.

The test piece, however, prepard in this Example is so unsatisfactory in stability as showed in Example 4 that it cannot be offered to users as goods.

EXAMPLE 1

One point five milligrams of 1-methoxy PMS, 1.5 g of gelatin, 8 mg of NAD, and 100 U of β-hydroxybutyric acid dehydrogenase (origin: *Rhodopseudomonas spheroides*) were dissolved in 10 ml of 0.1M tris-hydroxyaminomethanehydrochloric acid buffer solution (pH 8), and then 100 mg of nitro-TB was dissolved in the solution. Immediately, the solution was applied in uniform 0.4 mm thickness on polyester film using a doctor knife and dried at 25° C. for 2 hr.

The dried film was cut into a 5×7 mm test piece and adhered to an end of a 5×90 mm strip of PVC film to form a test strip. A drop of patient serum containing various concentration of β-hydroxybutyric acid was applied on the test piece of the test strip. After 2 min of reaction, excessive serum was lightly sucked up with absorptive paper. After further 3 min when the developed color was stabilized, it was compared by the naked eye with the standard color table, prepared in advance, showing the hue of developed color corresponding to 0, 0.1, 0.2, 0.5, 1.0, 2.0, 5.0, and 10.0 mmol/l of β-hydroxybutyric acid in the patient serum.

Table 2 shows the result of β-hydroxybutyric acid concentration determined by the method of the invention (measurement x) and by that described in Japanese Tokkai Sho 55-35232 specification (measurement y) on the same serum samples. Both the measurements show good correlationship with a correlation coefficient of 0.988 and regression line equation:

$$y = 1.06x - 0.02$$

TABLE 2

| Specimen No. | x | y | Specimen No. | x | y |
|---|---|---|---|---|---|
| 1 | 0.05 | 0.07 | 16 | 0.1 | 0.04 |
| 2 | 0.5 | 0.47 | 17 | 0.15 | 0.20 |
| 3 | 0.2 | 0.25 | 18 | 0.1 | 0.07 |
| 4 | 0.7 | 0.73 | 19 | 0.1 | 0.09 |
| 5 | 0.3 | 0.51 | 20 | 0.2 | 0.24 |
| 6 | 1.5 | 1.36 | 21 | 0.3 | 0.29 |
| 7 | 1.5 | 1.52 | 22 | 0.5 | 0.43 |
| 8 | 0.2 | 0.23 | 23 | 0.5 | 0.62 |
| 9 | 0.3 | 0.25 | 24 | 0.5 | 0.57 |
| 10 | 2.0 | 2.31 | 25 | 0.1 | 0.1 |
| 11 | 2.0 | 1.76 | 26 | 0.05 | 0.08 |
| 12 | 3.0 | 3.05 | 27 | 0.1 | 0.12 |
| 13 | 3.0 | 2.76 | 28 | 0.25 | 0.32 |
| 14 | 5.0 | 4.84 | 29 | 0.3 | 0.27 |
| 15 | 5.0 | 6.17 | 30 | 1.0 | 1.07 |

EXAMPLE 2

The composition of Reference Example 2 was added with 1 g of ethyl cellulose dissolved in 10 ml of chloroform and 1.5 ml of 20% aqueous gelatin solution, and formed W/O emulsion being dispersed by strong stirring. This emulsion was uniformly applied by use of a doctor blade 0.15 mm thick on polyester film, and gave porous semipermeable membrane after being dried for 45 min at 30° C.

The obtained membrane was processed into a tester similar to that in Reference Example 2. One drop of a whole blood sample was applied on the test piece of the test strip. When surplus sample was wiped off after 3 min with absorbent cotton, the corpuscle component was removed and blue-purple color corresponding to the concentration of β-hydroxybutyric acid in the whole blood was revealed.

EXAMPLE 3

A solution (1) was prepared by dissolving 120 mg of NAD, 4000 U of diaphorase, 60 mg of nitro-TB, 2000 U of β-hydroxybutyric acid dehydrogenase (origin: *Pseudomonas lemoignei*), and 1 g of gelatin in 10 ml of 0.2M-monopotassium phosphate—borax buffer solution (pH 8). To a solution (2) of 1 g of ethylcellulose dissolved in 10 ml of chloroform, 3.0 ml of the above solution (1) was added, and formed W/O emulsion being dispersed by strong stirring. This emulsion was uniformly applied by use of a doctor blade 0.15 mm thick on polyester film, and gave porous semipermeable membrane after being dried for 45 min at 30° C.

This test strip could measure the concentration of β-hydroxybutyric acid in the whole blood sample in 3 min according to the method showed in Example 2.

Since diaphorase was used as electron transporter in the composition of this Example, the composition had the conservative stability of 6 months at 25° C. Further, the concentration of β-hydroxybutyric acid in blood in the whole blood sample could be measured without making serum (or plasma) by separating corpuscles. The developed blue-purple color corresponding to the concentration of β-hydroxybutyric acid on the test surface was more uniform than that on a tester surface of paper carrier, a measurement result of high accuracy being acquired.

EXAMPLE 4

The results of the examination of conservative stability of the compositions prepared in Reference Example 2 and Example 1–3 (periods until the judgement of the concentration of β-hydroxybutyric acid became difficult because the test surfaces were colored dark blue-purple from original cream color) are showed in Table 3.

TABLE 3

| Tester | Store at 40° C. | 25° C. | 4° C. |
|---|---|---|---|
| Example 1 by Owen | 20 hrs | 14 days | 30 days |
| Reference Example 2 | 1 day | 7 days | 15 days |
| Example 1 | 2 days | 15 days | 3 months |
| Example 2 | 4 days | 30 days | 12 months |
| Example 3 | 4 days | 30 days | 15 months |

Compared with Example 1 by Owen, the stability of test pieces united in the presence of buffer also was nearly equal in Reference Example 2, improved in Example 1, and definitely better in Example 2 and 3. From the above results, the conservative stability is improved by adding a hydrophilic binder. Further, a stable composition usable as goods for determining β-hydroxybutyric acid can be prepared by applying and drying W/O emulsion formed by dispersing in a hydrophobic binder.

While the described Examples represent the preferred form of the invention, it is to be understood that the invention is not limited thereto and various modifications can be made without departing from the spirit of the invention. For example, proteins and polysaccharides are used as a stabilizer of enzyme and color producing agent and hydrazine compounds and magnesium compounds are used as a reaction accelerator. Various additives such as consistency agent and surfactant can also be used. The solvent may be various organic solvents, not only being water. Each material may be dispersed in the solvent in the form of suspension or emulsion, not necessarily be dissolved. Further, the invention can be applied to the quantitative analysis of β-hydroxybutyric acid in food additives and other specimens, in addition to the above described clinical examination field.

As detailed above, the invention comprises a uniform solid-phase composition of reagents by which β-hydroxybutyric acid can be determined, and also comprises a method for preparing the said composition. In the invention, β-hydroxybutyric acid is determined according to the following method.

β-Hydroxybutyric acid is dehydrogenated at pH 7–9 under the presence of NAD by β-hydroxybutyric acid dehydrogenase, NADH produced here reduces tetrazolium salt through an electron transporter into colored formazan in proportion to the quantity of β-hydroxybutyric acid, and the quantity of β-hydroxybutyric acid is determined by comparison of the developed color of formazan with the standard color table.

The method of the present invention, unlike the conventional methods, is very easy to use without requiring pretreatment of specimen (particularly blood), special equipment, complex operation, and special skill, and gives results in short time.

The composition of the invention realizes quick and simple operation and minimized the use of specimen, essential requirements for daily examination in the clinical field, requiring only one drop of specimen applied on the composition and completing the color development in several minutes. Particularly, in combination with the urine sugar and blood sugar test pieces available on the market, it permits measurement of both sugar and β-hydroxybutyric acid concentrations in urine and blood by similar operation. This is very convenient for doctors and nurses, and further for diabetes patients who have to be examined in their homes. Thus, the composition has very large practical value.

We claim:

1. A test indicator consisting essentially of:
    (a) a composition for determining beta-hydroxybutyric acid in a liquid, said composition consisting essentially of a single pH buffer for maintaining pH within the range of 7 to 9, beta-hydroxybutyric acid dehydrogenase, NAD (Nicotinamide adenine dinucleotide), diaphorase, and nitro-TB and a binder comprising a natural or synthesized film-forming polymer; and
    (b) a water-impermeable substrate on which said composition is applied;
    said indicator being a one-layered indicator on said substrate.

2. A method for preparing a test indicator for determining beta-hydroxybutyric acid in a liquid comprising:
    (a) uniformly applying on a water-impermeable substrate a water-in-oil emulsion said emulsion being prepared by dispersing a first solution in a second solution, said first solution being prepared by dissolving in water a single pH buffer for maintaining pH within the range of 7 to 9, beta-hydroxybutyric acid dehydrogenase, NAD (Nicotinamide adenine dinucleotide), diaphorase and nitro-TB and a binder comprising at least one natural or synthetic film-forming polymer; said second solution being prepared by dissolving at least one natural or synthetic film-forming polymer into a water-insoluble organic solvent; and
    (b) drying said emulsion.

3. The method of claim 2 wherein said nitro-TB is the last ingredient to be dissolved during preparation of said first solution.

* * * * *